(12) United States Patent
Huo et al.

(10) Patent No.: US 8,007,461 B2
(45) Date of Patent: Aug. 30, 2011

(54) STERILE DRUG-MIXING SYRINGE

(76) Inventors: Pingan Huo, Zhongshan (CN);
Wenqing Zhang, Zhongshan (CN);
Wuyuan Li, Zhongshan (CN); Yan Liu,
Zhongshan (CN); Xinming Wang,
Zhongshan (CN); Chunqing Jin,
Zhongshan (CN)

( * ) Notice: Subject to any disclaimer, the term of this patent is extended or adjusted under 35 U.S.C. 154(b) by 195 days.

(21) Appl. No.: 12/297,627

(22) PCT Filed: Sep. 12, 2006

(86) PCT No.: PCT/CN2006/002361
§ 371 (c)(1),
(2), (4) Date: Jul. 31, 2009

(87) PCT Pub. No.: WO2007/118372
PCT Pub. Date: Oct. 25, 2007

(65) Prior Publication Data
US 2009/0326448 A1 Dec. 31, 2009

(51) Int. Cl.
*A61M 37/00* (2006.01)
(52) U.S. Cl. .............................. 604/82; 604/88; 604/415
(58) Field of Classification Search .............. 604/82–92, 604/411, 413, 414–416
See application file for complete search history.

(56) References Cited

U.S. PATENT DOCUMENTS

| | | | |
|---|---|---|---|
| 3,336,924 A * | 8/1967 | Sarnoff et al. ................ | 604/415 |
| 3,872,867 A * | 3/1975 | Killinger ...................... | 604/413 |
| 3,995,630 A * | 12/1976 | van de Veerdonk .......... | 604/202 |
| 4,092,546 A * | 5/1978 | Larrabee ....................... | 250/515.1 |
| 4,328,802 A * | 5/1982 | Curley et al. ................. | 604/88 |
| 4,568,346 A * | 2/1986 | van Dijk ....................... | 604/414 |
| 2003/0055376 A1* | 3/2003 | Delay ............................ | 604/82 |
| 2005/0113747 A1* | 5/2005 | Moir .............................. | 604/87 |
| 2008/0177226 A1* | 7/2008 | Watanabe et al. ............. | 604/92 |
| 2008/0188799 A1* | 8/2008 | Mueller-Beckhaus et al. . | 604/88 |

FOREIGN PATENT DOCUMENTS

| | | |
|---|---|---|
| CN | 2745587 Y | 12/2005 |
| CN | 2748095 Y | 12/2005 |
| WO | 2005089837 A1 | 9/2005 |

* cited by examiner

*Primary Examiner* — Nicholas D Lucchesi
*Assistant Examiner* — Quynh-Nhu H Vu
(74) *Attorney, Agent, or Firm* — Knoble Yoshida & Dunleavy, LLC

(57) ABSTRACT

The invention is directed to a menstruum prepositioned type sterile drug-mixing syringe and a menstruum separately positioned type sterile drug-mixing syringe including a shell, a needle, a piston and a push-pull rod assembly. The syringe further includes a menstruum bottle, a solute bottle, a sliding sleeve and a needle loading assembly. The menstruum bottle may be fixed to the inner wall of a sliding sheath, and the solute bottle may be fixed to the inner of the shell. Piston may be disposed within the solute bottle. The sliding sleeve may be socketed to the front end of the shell in advance or disposed by other ways. The mouth of the menstruum bottle may be opposite to the mouth of the solute bottle and may be connected by a needle, which has two piercing tips, wherein the needle punctures and is securely connected to the needle loading assembly.

10 Claims, 6 Drawing Sheets

US 8,007,461 B2

STERILE DRUG-MIXING SYRINGE

CROSS REFERENCES TO RELATED APPLICATIONS

This is a U.S. National Stage Application which claims the benefit of priority, under 35 U.S.C. §356(c) to International Patent Application No. PCT/CN2006/001361, filed on Sep. 12, 2006, which in turn claims priority to Chinese Patent Application Nos. CN 200610042690.2, filed on Apr. 18, 2006, CN 200620078828.X, filed on Apr. 18, 2006 and CN 200620079041.5, filed on May 25, 2006, the entire disclosures of which are incorporated by reference herein.

BACKGROUND OF THE INVENTION

1. Field of the Invention

The present invention pertains to a syringe for medical use. Specifically, the syringe may be a preassembled drug-mixing syringe comprising a menstruum bottle, a solute bottle and a syringe or alternatively a separately assembled drug-mixing syringe.

2. Description of the Related Art

In general, pre-charged syringes are beneficial because they simplify the injection process and more importantly, avoid the occurrence of possible medical accidents caused by mixing the wrong drugs. They also advantageously enable automatic injection and are convenient to use. In most prior art pre-charged syringes, the menstruum vial disadvantageously contacts the push pull of the syringe, and the solute cartridge is positioned in the front of the syringe. The drug mixing operation is achieved when the menstruum is pressurized and forced into the solute cartridge through a communicating needle; the mixed drug solution is subsequently pushed out of the solute cartridge. Typically, these syringes have multiple components and complicated designs. For example, they generally require two needles, an injection needle and a communication needle, which complicates and increases the cost of manufacturing. Although these pre-charged syringes provide certain advantages in comparison to conventional syringes, further improvements are necessary to create an efficient and effective drug-mixing syringe. Therefore, there is a need to develop a drug-mixing syringe that will simplify the drug mixing procedure as well as have a simplified syringe structure and further facilitate packaging.

SUMMARY OF THE INVENTION

It is an object of the present invention to overcome the disadvantages of existing pre-charged type syringes by providing a drug-mixing syringe which preassembles the menstruum bottle, solute bottle and syringe in order to make the injection operation simple, convenient and fast.

It is another object of the present invention to provide an unassembled drug-mixing syringe that simplifies injection and also reduces the packaging size so that the syringe is more convenient to carry.

The objects of the menstruum prepositioned type sterile drug-mixing syringe according to the present invention are achieved by the following technical solutions:

A drug-mixing syringe comprising: a shell, wherein said shell comprises a hollow cylinder shell housing; a needle positioned in a proximal end of the shell, wherein said needle comprises two piercing tips, a first bottle for containing a powder wherein said first bottle is located within a distal end of the shell and wherein said first bottle comprises a first opening; a piston located in a distal opening of the shell, wherein said piston is slidably received within a distal end of said first bottle; a push-pull assembly connected to the piston: a sliding sleeve that slidably receives the shell and wherein said sliding sleeve comprises a hollow cylinder sliding sleeve housing; a second bottle for containing a menstruum, wherein said second bottle is located within a proximal end of the sliding sleeve, wherein said second bottle comprises a second opening, and wherein said first openings and said second opening face one another; and a needle loading assembly that connects said first opening to said second opening, wherein the needle loading assembly is fixedly coupled to the needle.

A drug-mixing syringe assembly comprising: a first syringe component comprising: a shell, wherein said shell comprises a hollow cylinder shell housing; a needle positioned in a proximal end of the shell, wherein said needle comprises two piercing tips; a first bottle for containing a powder, wherein said first bottle is fixed within a distal end of the shell and wherein said first bottle comprises an opening; and a piston located in a distal opening of the shell, wherein said piston is slidably received within a distal end of said first bottle; push-pull assembly connected to the piston; and a needle loading assembly fixedly coupled to the needle, wherein said first bottle is slidably received within a distal end of the needle loading assembly; and a second syringe component comprising:

a second bottle for containing a menstruum, wherein said first syringe component may be removably attached to said second syringe component.

BRIEF DESCRIPTION OF THE DRAWINGS

FIG. 4 is also a cross-sectional view of a separately assembled drug-mixing syringe wherein the menstruum bottle is removed and the second stage push-pull member is pulled out from the first stage push-pull member after drug mixing is completed.

DETAILED DESCRIPTION OF THE PREFERRED EMBODIMENTS

Figure 1:
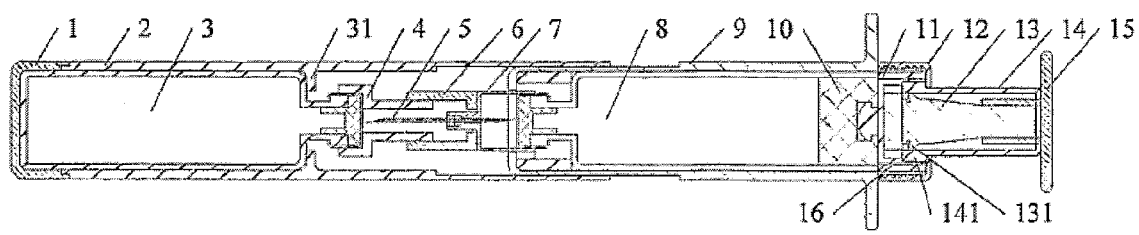
FIG. 1 is a cross-sectional view showing one embodiment of a preassembled drug-mixing syringe in a first position.

The invention is directed to novel syringes, specifically sterile drug-mixing syringes. In an exemplary embodiment, the invention may be directed to a preassembled sterile drug-mixing syringe and an unassembled drug-mixing syringe. The exemplary embodiments according to the present invention will be described with reference to the accompanying drawings.

1. Menstruum Prepositioned Type Sterile Drug-Mixing Syringe

Referring to FIGS. 1-11, the preassembled drug-mixing syringe of the present invention comprises a sliding sleeve 2, a menstruum bottle 3, a solute bottle 8, a piston 10, a shell 9, a needle 5, a needle loading assembly and a push-pull assembly.

Sliding sleeve 2 may be a hollow cylinder with an end cap 1 located on its front end. Sliding sleeve 2 may further include a circular bulge or protrusion 31 located in a middle region of and on an inner surface of sliding sleeve 2. Menstruum bottle 3 may be a vial that is sealed within sliding sleeve 2 via end cap 1, which is screwed to or tightly coupled to sliding sleeve 2. The mouth of the menstruum bottle 3 may face backward towards the push-pull assembly, and a shoulder of menstruum bottle 3 may rest against circular bulge 31.

Solute bottle 8 may be a cartridge or vial, and piston 10 may be positioned inside an opening located at a back end of solute bottle 8.

Shell 9 may be a hollow cylinder having a circular step formed on an inner surface of and located on a front end of shell 9. The solute bottle 8 may be positioned within shell 9 such that its mouth faces forward towards menstruum bottle 3 and such that its shoulder rests against the circular bulge of shell 9. The front end of shell 9 may be slidably socketed with, i.e. engaged with or received in as shown in FIG. 1, the rear opening of sliding sleeve 2 such that the mouth of the menstruum bottle 3 faces the mouth of solute bottle 8 and such that a needle loading assembly connects and enables communication between the mouths. of menstruum bottle 3 and solute bottle 8.

The needle 5 may be a communicating needle having piercing tips at both ends. Needle 5 may pierce and may be fixed to the needle loading assembly.

In one embodiment, the needle loading assembly may include a sliding support member 4, a middle support member 6 and a needle support member 7.

Figure 7:
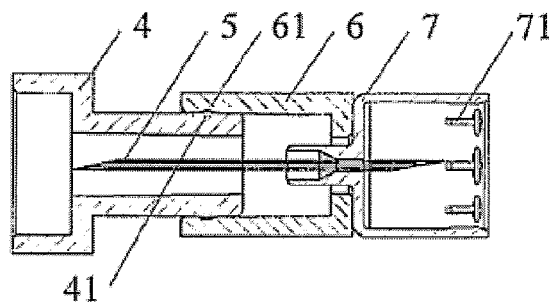
FIG. 7 is a cross-sectional view showing the needle loading assembly of the preassembled drug-mixing syringe in an initial position.

Sliding support member 4 may include two hollow cylinder sections having different diameters. The front section may have a larger diameter than the rear section. Sliding support member 4 may also have a step formed where the two sections are joined. A protrusion or circular bulge 41 may be formed on the outer surface of and near a back end of sliding support member 4. The mouth of menstruum bottle 3 tightly engages with the front inner wall of sliding support member 4 and is restricted by the inner surface of the circular step of sliding support member 4. The outer surface of the rear portion of sliding support member 4 may be slidably socketed with, i.e. engaged with or received in as shown in FIG. 7, the inner surface of the front portion of the middle support member 6.

The middle support member 6 may be a hollow cylinder having an indentation or circular groove 61 to engage circular bulge 41 formed on the outer surface of the rear portion of sliding support member 4. The rear end of the middle support member 6 may coaxially contact the closed end of needle support member 7.

Figure 2:
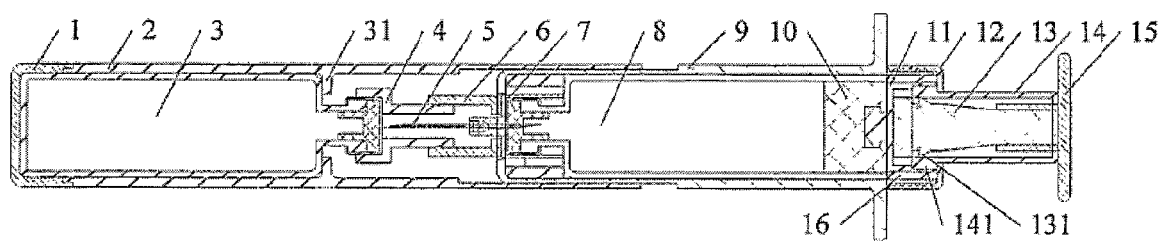
FIG. 2 is a cross-sectional view of the preassembled drug-mixing syringe showing the needle piercing the rubber stopper of the solute bottle.
Figure 8:
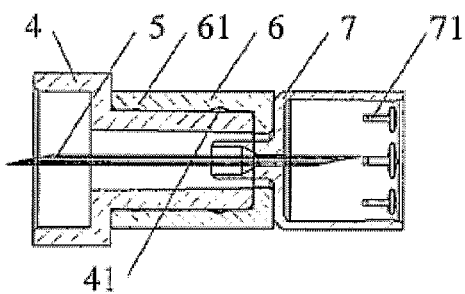
FIG. 8 is a cross-sectional view showing the needle loading assembly of the preassembled drug-mixing syringe in a drug mixing position.
Figure 9:
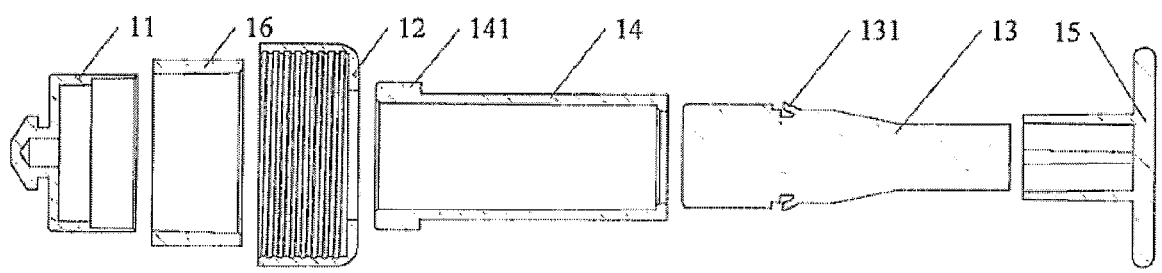
FIG. 9 is a cross-sectional view showing the components of the push-pull assembly of the preassembled and separately assembled drug-mixing syringe.

Needle support member 7 may be a hollow cylinder having a closed front end. A bore may be formed in the centre of the closed front end, through which needle 5 passes, wherein needle 5 may be fixed to needle support member 7. The rear end of needle support member 7 may be slidably socketed with, i.e. receive or engaged with as shown in FIG. 2, the mouth of the solute bottle 8. A non-return mechanism, for example a retention member such as claws 71, as shown in FIG. 8, claws 71 may be formed on the inner wall of the rear end of needle support member 7. Claws 71 may engage the backside of the mouth of solute bottle 8 after it reaches the closed end of the needle support member 7 from the rear end of the needle support member 7.

The push-pull assembly comprises a first stage push-pull member 14, a second stage push-pull member 13, a handle 15 and a fixing sleeve 12. In an exemplary embodiment the push-pull assembly may operate by applying a pushing force, a pulling force or a pushing force followed by a pulling force.

First stage push-pull member 14 may be a hollow cylinder having a protruding step 141 formed on the outer surface of first stage push-pull member 14 at its front end. Fixing sleeve 12 may engage step 141 and may be screwed to the rear end of the shell 9 so as to coaxially fix the first stage push-pull member 14 to the rear end of shell 9. An indenter 11 having an outer diameter that is slightly smaller than the inner diameter of solute bottle 8 may be tightly coupled to the front end of the first stage push-pull member 14. A central protruding end of indenter 11 may be embedded in the rear end of piston 10. A positioning ring 16 covers at least a portion of indenter 11 and has an outer diameter equal to or slightly smaller than the inner diameter of shell 9.

Figure 10:
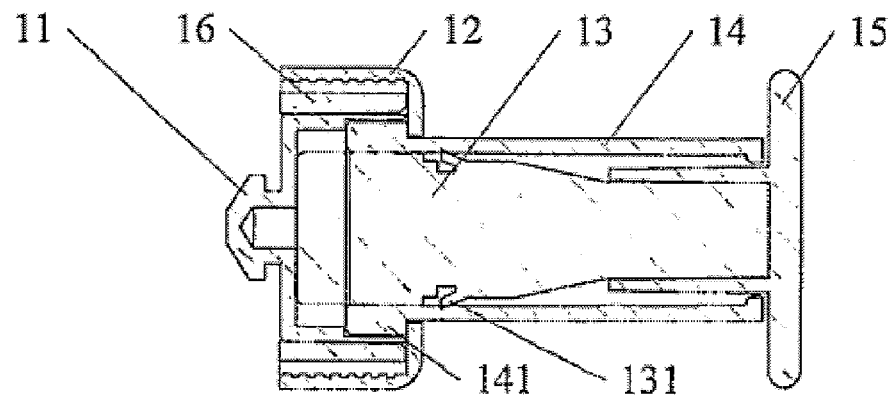
FIG. 10 is a cross-sectional view showing the push-pull assembly of the preassembled and separately assembled drug-mixing assembly in an initial stage.
Figure 11:
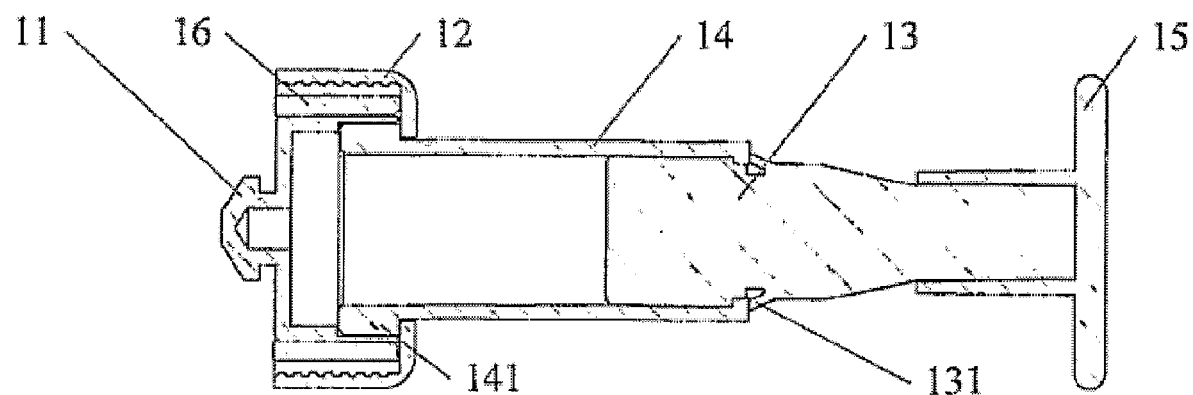
FIG. 11 is a cross-sectional view showing the push-pull assembly of the preassembled and separately assembled drug-mixing assembly wherein the second stage push-pull member is pulled out from the first stage push-pull member.

The cross section of the second stage push-pull member 1.3 may have a shape similar to a "+" symbol, "Y" symbol or tubular structure. The second stage push-pull member 13 may be slidably socketed with, i.e. engaged with or received in as shown in FIG. 10, first stage push-pull member 14. Claws 131 may be formed on an outer surface of and near the front portion of second stage push-pull member 13. The rear end of the second stage push-pull member 13 may be fixedly coupled to the handle 15.

Before leaving the factory, menstruum bottle 3 may be pre-charged and sealed with a pre-determined amount of menstruum, such as water for injection, and pressurized using compressed air. Solute bottle 8 may also be pre-charged and sealed with a powder or liquid drug of a predetermined dosage. FIG. 1 shows the drug-mixing syringe at this initial stage wherein menstruum bottle 3 and/or solute bottle 8 are pre-charged. As shown in FIG. 7, sliding support member 4, middle support member 6 and needle support member 7 of the needle loading assembly are in an initial first position. Circular bulge 41 on the outer surface of sliding support member 4 engages with circular groove 61 located on the inner wall of middle support member 6. The mouth of the solute bottle 8 is located in a rear portion of the needle support member 7, but solute bottle 8 does not completely pass through claws 71 formed on the inner wall of the needle support member 7. At this time, needle 5 does not enable communicating between menstruum bottle 3 and solute bottle 8. FIG. 10 shows the push-pull assembly is now in its initial first position. The overall length of the push-pull assembly is minimized as the second stage push-pull member 13 is completely socketed within the first stage push-pull member 14. At this time, claws 131 are inactive.

Figure 3:
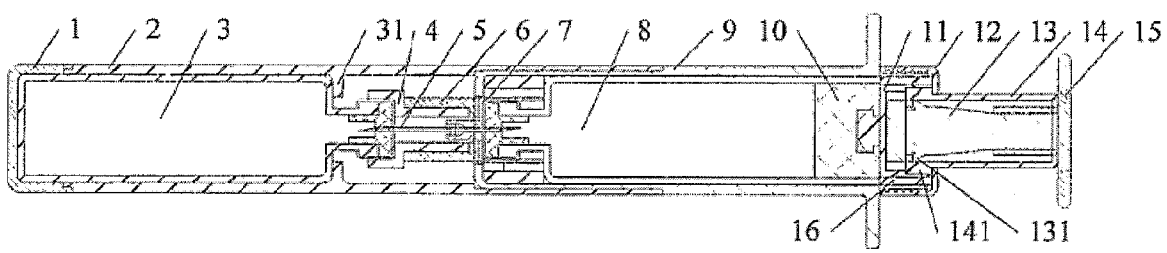
FIG. 3 is a cross-sectional view of the preassembled drug-mixing syringe showing the two ends of the needle piercing the rubber stoppers of the solute bottle and the menstruum bottle to initiate drug mixing.

Prior to injection, the front end of the drug-mixing syringe is pointed upward such that the syringe is upright and the mouth of menstruum bottle 3 in the sliding sleeve 2 points downward. Sliding sleeve 2 may be subsequently pushed downward so that menstruum bottle 3 will consequently apply a pressure to and induce the sliding support member 6 of the needle loading assembly to move. Because circular bulge 41 of the sliding support member 4 is engaged with circular groove 61 of middle support member 6, the middle support member 6 is forced to move. The middle support member 6 consequently forces the needle support member 7 to move downward, so that the lower end of needle 5 fixed to needle support member 7 pierces through the rubber stopper of solute bottle 8, as shown in FIG. 2. At this time the inner end of needle support member 7 is biased against the mouth of solute bottle 8, and claws 71 inside needle support member 7 engages with the backside of the mouth of solute bottle 8. Sliding sleeve 2 may be further pushed downward so that it slides along the outer wall of shell 9 until sliding sleeve 2 reaches a point where it can no longer move. At this time, circular bulge 41 of the sliding support member 4 disengages with the circular groove 61 of the middle support member 6, and the outer surface of the circular step of sliding support member 4 becomes biased against the front end of the middle support member 6, as shown in FIG. 8. The upper end of needle 5 may then pierce through the rubber stopper of menstruum bottle 3 so that menstruum bottle 3 communicates with solute bottle 8, as shown in FIG. 3. The liquid menstruum in pressurized menstruum bottle 3 enters solute bottle 8 through needle 5, mixing with and dissolving the powder drug contained in solute bottle 8.

Figure 4:
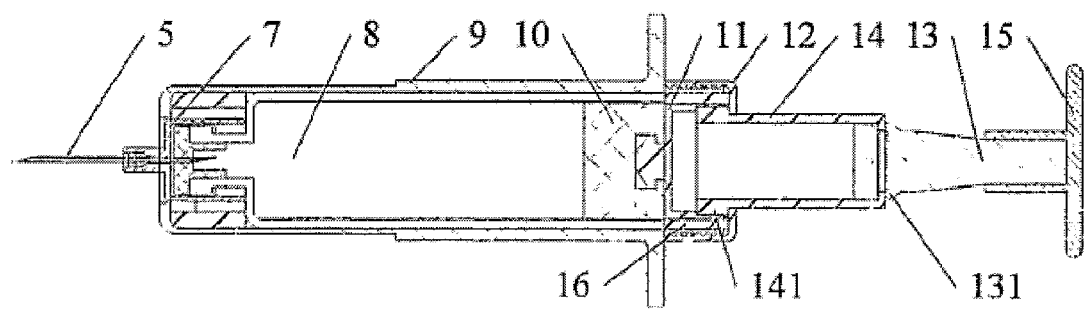
FIG. 4 is a cross-sectional view of the preassembled drug-mixing syringe wherein the sliding support member and the middle support member is removed and wherein the second stage push-pull member is pulled out from the first stage push-pull member after drug mixing has been completed.

When the drug mixing operation is completed, sliding sleeve 2 may be removed so that sliding support member 4 and middle support member 6 disengages with shell 9. Needle support member 7 does not disengage with shell 9 because claws 71 of needle support member 7 engages with the backside of the mouth of solute bottle 8. Additionally, the lower end of needle 5 is not removed from the rubber stopper of solute bottle 8. At this time, the upper end of needle 5 is fully exposed. Handle 15 may be extended downward so that the second stage push-pull member 13 will slide downward with respect to the first stage push-pull member 14 until claws 131 of the second stage push-pull member 13 engages the rear end of the first stage push-pull member 14, as shown in FIG. 4. Pressure may be subsequently applied to handle 15 in order to remove air from inside solute bottle 8 by moving piston 10 via second stage push-pull member 13, first stage push-pull member 14 and indenter 11. The mixed and dissolved drug solution may then be injected into a human through needle 5.

Menstruum bottle 3 need not be pressurized. When menstruum bottle 3 is not pressurized, the second stage push-pull member 13 may be pulled out in advance. Pressure may be applied to handle 15 to make indenter 11 move piston 10 upward. When menstruum bottle 3 and solute bottle 8 are in communication with one another, as shown in FIG. 3, handle 15 may be pulled downward inducing piston 10 to move downward so that the menstruum contained in menstruum bottle 3 is drawn into solute bottle 8 for drug mixing.

2. Menstruum Separately Positioned Type Sterile Drug-Mixing Syringe

In a second exemplary embodiment, an unassembled or separately assembled drug-mixing syringe of the present invention may be similar to the preassembled drug-mixing syringe embodiment described above. Referring to FIGS. 12-16 and 4-5, the separately assembled drug-mixing syringe of the present invention comprises a sliding sleeve 2, a menstruum bottle 3, a solute bottle 8, a piston 10, a shell 9, a needle 5, a needle loading assembly and a push-pull assembly. The differences between these two embodiments are discussed below.

Figure 12:
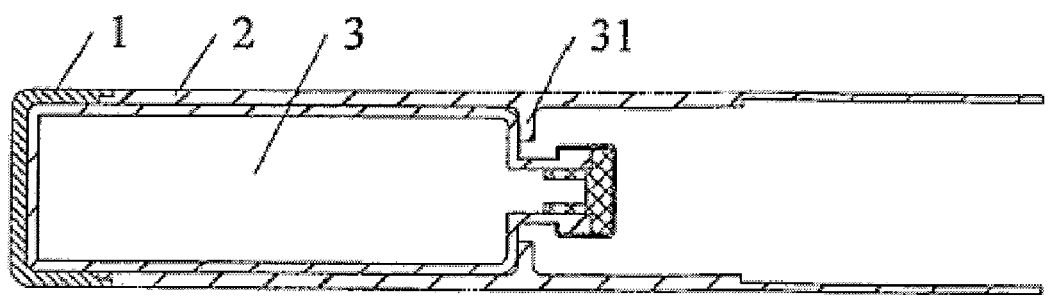
FIG. 12 is a perspective view of a second embodiment showing the menstruum bottle in the sliding sleeve of a separately assembled drug-mixing syringe.
Figure 16:
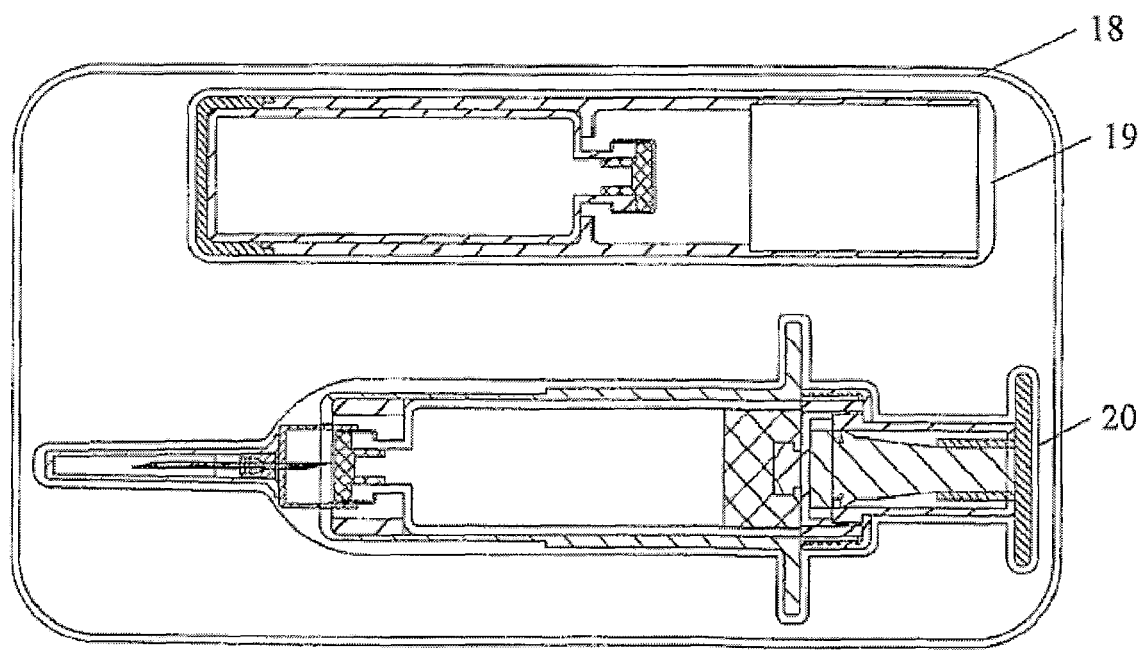
FIG. 16 is a cross-sectional view showing the packaged separately assembled drug-mixing syringe of the second embodiment.

In the separately assembled drug-mixing syringe of FIG. 12, sliding sleeve 2 containing menstruum bottle 3 is not socketed with the shell 9. Rather, as shown in FIG. 16, sliding sleeve 2 is placed within recess 19 of packaging 18. Other syringe components may be placed in recess 20 of packaging 18.

Figure 13:
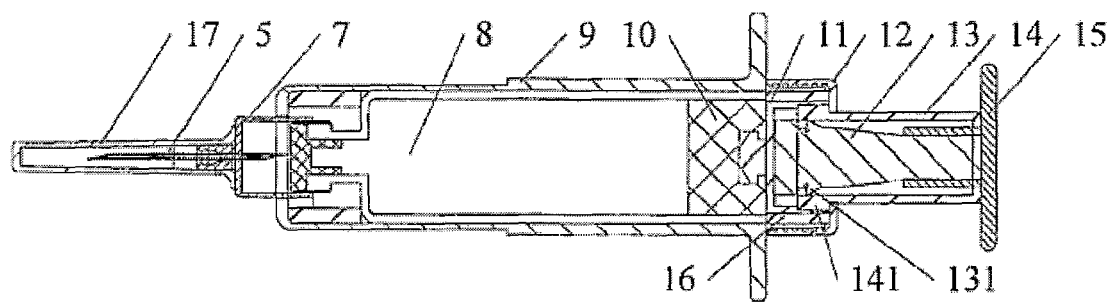
FIG. 13 is a cross-sectional view showing the separately assembled sterile drug-mixing syringe without the menstruum bottle and the sliding sleeve.

The needle loading assembly may include only a needle support member 7. The sliding support member 4 and the middle support member 6 may be omitted. As shown in FIG. 13, the exposed end of the needle 5 may be covered with a needle jacket 17.

The other components of the separately assembled drug-mixing syringe may be identical to the components of the preassembled drug-mixing syringe in their shapes, structures, sizes and configurations.

Figure 5:
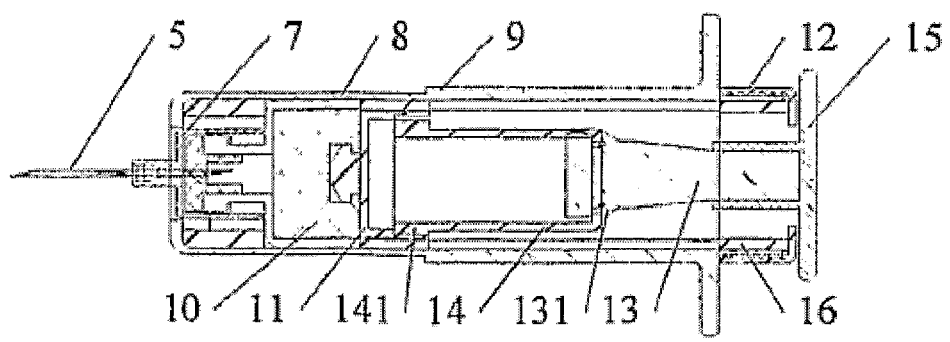
FIG. 5 is a cross-sectional view of the preassembled and separately assembled drug-mixing syringe after injection is completed.
Figure 6:
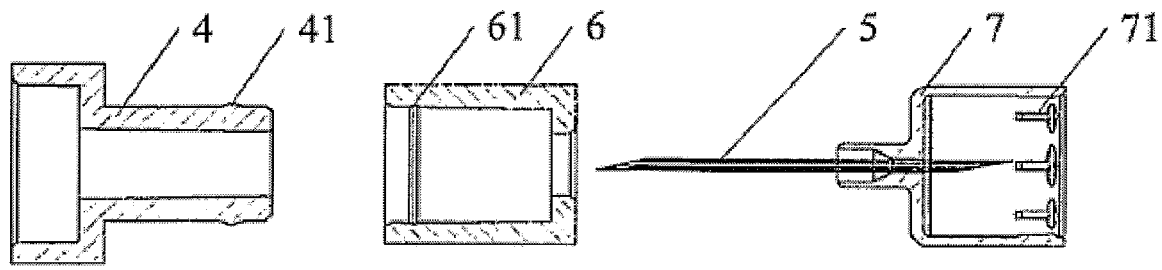
FIG. 6 is a cross-sectional view showing the components of the needle loading assembly of the preassembled drug-mixing syringe.
Figure 14:
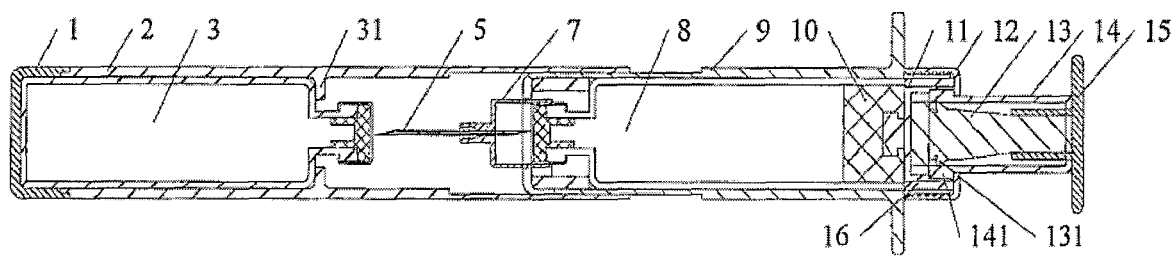
FIG. 14 is a perspective view of the separately assembled drug-mixing syringe showing the sliding sleeve containing the menstruum bottle attached to the front of the syringe.
Figure 15:
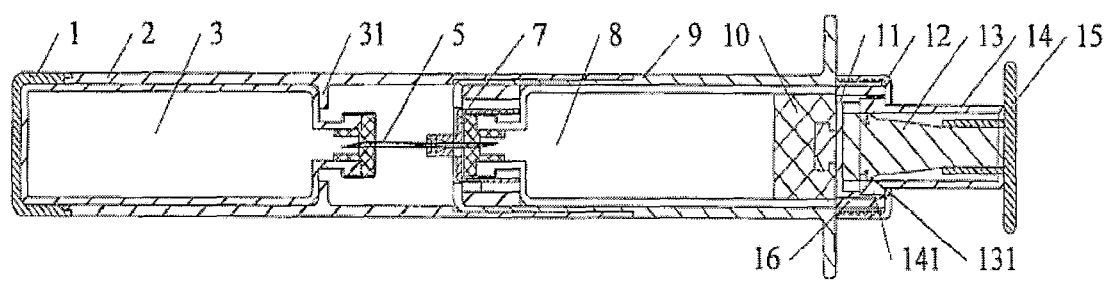
FIG. 15 is a cross-sectional view of the separately assembled drug-mixing syringe showing the two ends of the needle piercing the rubber stoppers of the solute bottle and the menstruum bottle to initiate drug mixing.

Before injection, sliding sleeve 2 containing the menstruum bottle 3 and the other parts of the syringe may be removed from packaging 18, and needle jacket 17 may be removed from needle 5. The rear opening of the sliding sleeve 2 may be socketed into, i.e. engaged with or received in as shown in FIG. 14, the front portion of shell 9. The mouth of menstruum bottle 3 may be oriented downward, and pressure may be applied to sliding sleeve 2 until the two ends of the needle 5 pierces the rubber stoppers of menstruum bottle 3 and solute bottle 8. The subsequent process of drug mixing and injection may be identical to the operations set forth for the preassembled drug-mixing syringe. As shown in FIG. 4, after mixing, sliding sleeve 2 may be removed from syringe assembly. The contents of the syringe assembly may then be injected, as depicted in FIG. 5.

In one embodiment, sliding sleeve 2 may also be omitted. The mouth of menstruum bottle 3 can be directly pointed towards the front end of needle 5 and may be pushed to complete the drug mixing operation. Then menstruum bottle 3 may be removed from the drug-mixing syringe assembly for the air removing and the injection operation.

Menstruum bottle 3 is need not be pressurized. When menstruum bottle 3 is not pressurized, the second stage push-pull member 13 may be pulled out in advance. Pressure may be applied to handle 15 to make indenter 11 move piston 10 upward. When the two bottles are in communication, handle 15 may be pulled downward inducing piston 10 to move downward so that the menstruum contained in menstruum bottle 3 is drawn into solute bottle 8 for drug mixing. Menstruum bottle 3 may then be removed for air discharging and injection operation.

Exemplary embodiments of the present invention have been disclosed herein and, it will be understood by those of ordinary skill in the art that various changes in form and details may be made without departing from the spirit and scope of the present invention as set forth in the following claims.

The preassembled drug-mixing syringe and the separately assembled drug-mixing syringe overcome the shortcomings of the existing syringe for medical use, having at least the following advantages over prior art:

1. The menstruum bottle, the solute bottle and the syringe of the preassembled drug-mixing syringe form a whole part thus simplifying the drug-mixing and the drug-adding procedure to shorten the preparation time, which is crucial for emergency cases.

2. Similarly, the solute bottle and the syringe of the separately assembled drug-mixing syringe also form a whole part thus simplifying the drug-mixing and the drug-adding procedure to shorten the preparation time.

3. The preassembled drug-mixing syringe and the separately assembled drug-mixing syringe are easy to carry, simple to use and self-rescuing not only in hospitals, but also outside hospitals, such as in the battlefield or in during transit, such as in moving vehicles, airplanes, vessels, etc.

4. The needle loading assembly is simplified and manufacturing cost is lowered by omitting the communicating needle.

5. The compact two stage push-pull member structure reduces the overall length of the syringe and the packing size. At the same time the maximum travel of the piston is satisfied to ensure all drug solution can be pushed out.

6. The separately assembled menstruum bottle and the simplified one-needle support structure further shortens the overall length of the syringe, making it more easy to pack and carry.

7. The structure, applicability and the cost effectiveness of the present invention meets the requirements of the development of the industry, and the structure of the drug-mixing syringe is novel.

8. The structure of the syringe of the present invention is technically more advantageous to the existing syringes. The unique structure and function of the present invention is better than and non-obvious with respect to the existing syringes. Therefore the present invention is inventive.

9. As experienced in researching, designing and manufacturing of medical equipment, the applicant of the invention is very familiar with the defects of the syringes for medical use and the present invention is proposed in view of such defects to achieve the expected objects and functions. Therefore the present invention has industrial applicability.

What is claimed is:

1. A drug-mixing syringe comprising:
   a shell, wherein said shell comprises a hollow cylinder shell housing;
   a needle positioned in a proximal end of the shell, wherein said needle comprises two piercing tips;
   a first bottle for containing a powder wherein said first bottle is located within a distal end of the shell and wherein said first bottle comprises a first opening;
   a piston located in a distal opening of, the shell, wherein said piston is slidably received within a distal end of said first bottle;
   a push-pull assembly connected to the piston;
   a sliding sleeve that slidably receives the shell and wherein said sliding sleeve comprises a hollow cylinder sliding sleeve housing;
   a second bottle for containing a menstruum, wherein said second bottle is located within a proximal end of the sliding sleeve, wherein said second bottle comprises a second opening, and wherein said first openings and said second opening face one another; and
   a needle loading assembly that connects said first opening to said second opening, wherein
   the needle loading assembly is fixedly coupled to the needle.

2. The drug-mixing syringe of claim 1, wherein the needle loading assembly comprises:
   a sliding support member, wherein said sliding support member comprises:
   a first hollow cylinder sliding support section and a second hollow cylinder sliding support section, wherein a diameter of the first hollow cylinder sliding support section is greater than a diameter of the second hollow cylinder sliding support section;
   a first circular step that joins the first and second hollow cylinder sliding support sections, wherein the circular step and a proximal end of the sliding support member engages the second opening of the second bottle; and
   a first positioning mechanism;
   a middle support member, wherein said middle support member comprises:
   a hollow cylinder middle support housing; and
   a second positioning mechanism for engaging the first positioning mechanism,
      wherein a distal end of the sliding support member is received within a proximal end of the middle support member; and
   a needle support member, wherein the needle support member comprises:
   a hollow cylinder needle support housing; and
   a retention mechanism formed on an inner surface of a distal end of the needle support member,
      wherein a proximal end of the needle support member comprises a bore which fixedly retains the needle support member,
      wherein the first bottle is slidably received within a distal end of the needle support member, and
      wherein a proximal end of the needle support member coaxially contacts a distal end of the middle support member.

3. The drug-mixing syringe of claim 2, wherein said first positioning mechanism is a circular bulge or groove, wherein said second positioning mechanism is a circular bulge or groove and wherein said first positioning mechanism slidably engages said second positioning mechanism.

4. The drug-mixing syringe of claim 2, wherein said first positioning mechanism is a protrusion or indent, wherein said second positioning mechanism is a protrusion or recess and wherein said first positioning mechanism slidably engages said second positioning mechanism.

5. The drug-mixing syringe of claim 2, wherein the retention mechanism is selected from the group consisting of at least one claw, at least one collar or a combination thereof.

6. The drug-mixing syringe according to claim 1, wherein the push-pull assembly comprising:
   a first stage push-pull member, wherein the first stage push-pull member comprises:
   a hollow cylinder first stage push-pull housing; and
   a second circular step that protrudes outward from a proximal end of the first stage push-pull member;

a second stage push-pull member, wherein the second stage push-pull member comprises:
  a second stage push-pull housing; and
  a claw located on a proximal end of the second stage push-pull housing,
    wherein said second stage push-pull member is slidably received within the first stage push pull member
a handle fixedly connected to a distal end of the second stage push-pull member; and
a fastener sleeve coupled to a distal end of the shell so as to coaxially fix the first stage push-pull member to the distal end of the shell, wherein the distal end of the fastener sleeve contacts the second circular step of the first stage push-pull member.

7. The drug-mixing syringe of claim 6, further comprising an indenter for coupling said push-pull assembly to said piston comprising:
  an indenter housing comprising an outer diameter smaller than an inner diameter of the first bottle; and
  a protrusion located on a proximal end of the indenter that is located in a distal end of the piston,
    wherein the indenter is coupled to the proximal end of the first stage push-pull member.

8. The drug-mixing syringe of claim 7, further comprising a ring component that surrounds a portion of the indenter, wherein the rims component comprises an outer diameter equal to or slightly smaller than an inner diameter of the shell.

9. The drug-mixing syringe of claim 1, wherein the second bottle contains a liquid menstruum and compressed air.

10. The drug-mixing syringe of claim 1, wherein the second bottle further comprises a shoulder and wherein the drug-mixing syringe further comprises:
  a cap connected to a proximal end of the sliding sleeve; and
  a protrusion located on an inner wall of sliding sleeve for retaining a shoulder of the second bottle.

* * * * *